United States Patent [19]

Kjellin et al.

[11] Patent Number: 4,546,182
[45] Date of Patent: Oct. 8, 1985

[54] 3,8-DIALKYLXANTHINES

[75] Inventors: Per G. Kjellin, Lund; Carl G. A. Persson, Löberöd, both of Sweden

[73] Assignee: Aktiebolaget Draco, Lund, Sweden

[21] Appl. No.: 523,731

[22] Filed: Aug. 16, 1983

Related U.S. Application Data

[63] Continuation-in-part of Ser. No. 248,995, Mar. 30, 1981, abandoned.

[30] Foreign Application Priority Data

Apr. 18, 1980 [SE] Sweden ................. 8002910

[51] Int. Cl.[4] .................... C07D 473/06; A61K 31/52
[52] U.S. Cl. .................... 544/273; 544/267;
[58] Field of Search .................... 424/253; 544/267

[56] References Cited

U.S. PATENT DOCUMENTS 4,089,959  5/1978  Diamond ................. 424/253
4,233,303  11/1980  Bergstrand et al. ........ 424/253
4,325,956  4/1982  Kjellin et al. ............. 424/253

FOREIGN PATENT DOCUMENTS 74004469  2/1974  Japan .

Primary Examiner—Nicholas S. Rizzo
Attorney, Agent, or Firm—Brumbaugh, Graves, Donohue & Raymond

[57] ABSTRACT

The invention refers to compounds having activity against chronic obstructive airway disease or cardiovascular disease, characterized by the formula

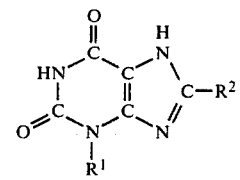

wherein $R^1$ is ethyl, n-propyl, n-butyl, isobutyl, n-pentyl, 2-methylbutyl, 3-methylbutyl, 2,2-dimethylpropyl, cyclopropyl, cyclobutyl, cyclopentyl or cyclohexylmethyl, and $R^2$ is methyl, ethyl, n-propyl, isopropyl, cyclopropyl, n-butyl, isobutyl, tert. butyl, or cyclobutyl provided that $R^1$ is ethyl when $R^2$ is methyl, or a physiologically acceptable salt thereof. The invention also refers to processes for the preparation of these compounds, a pharmaceutical preparation containing one of the compounds and a method for the treatment of chronic obstructive airway disease and cardiovascular disease.

4 Claims, 2 Drawing Figures

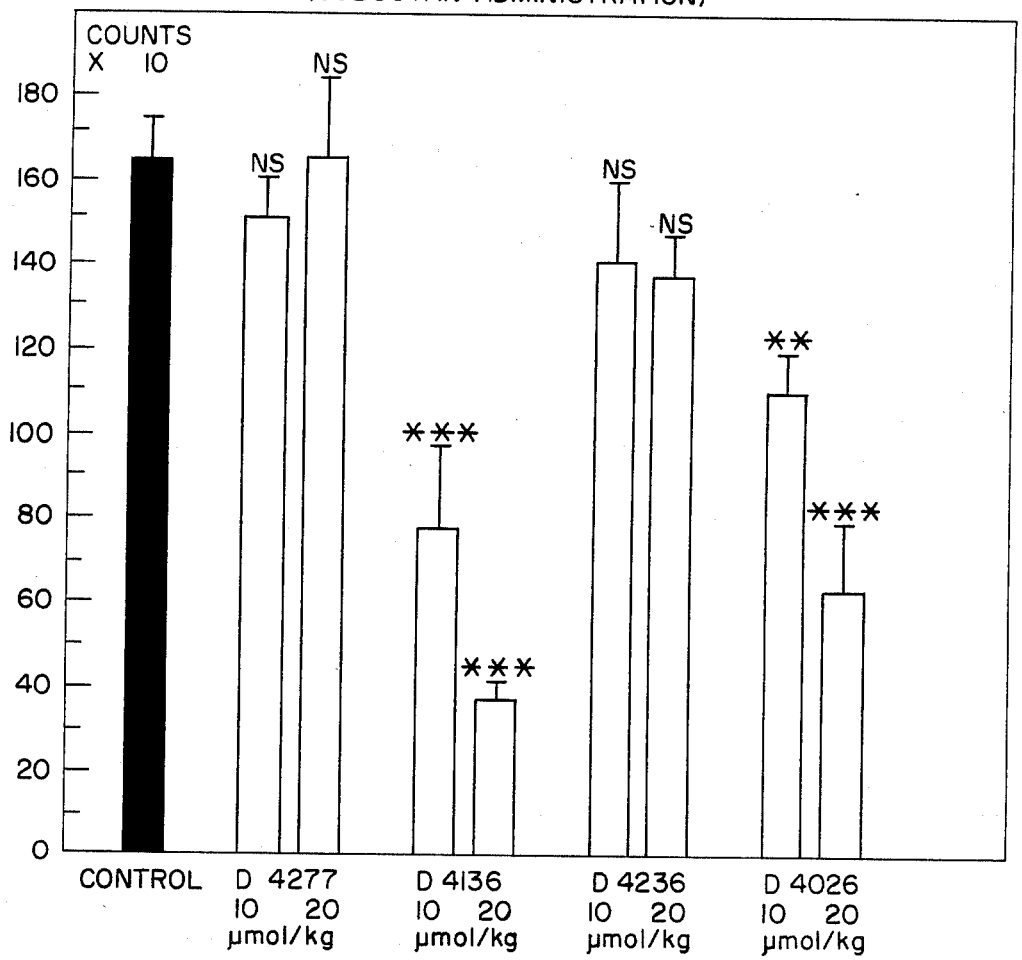
FIG. A

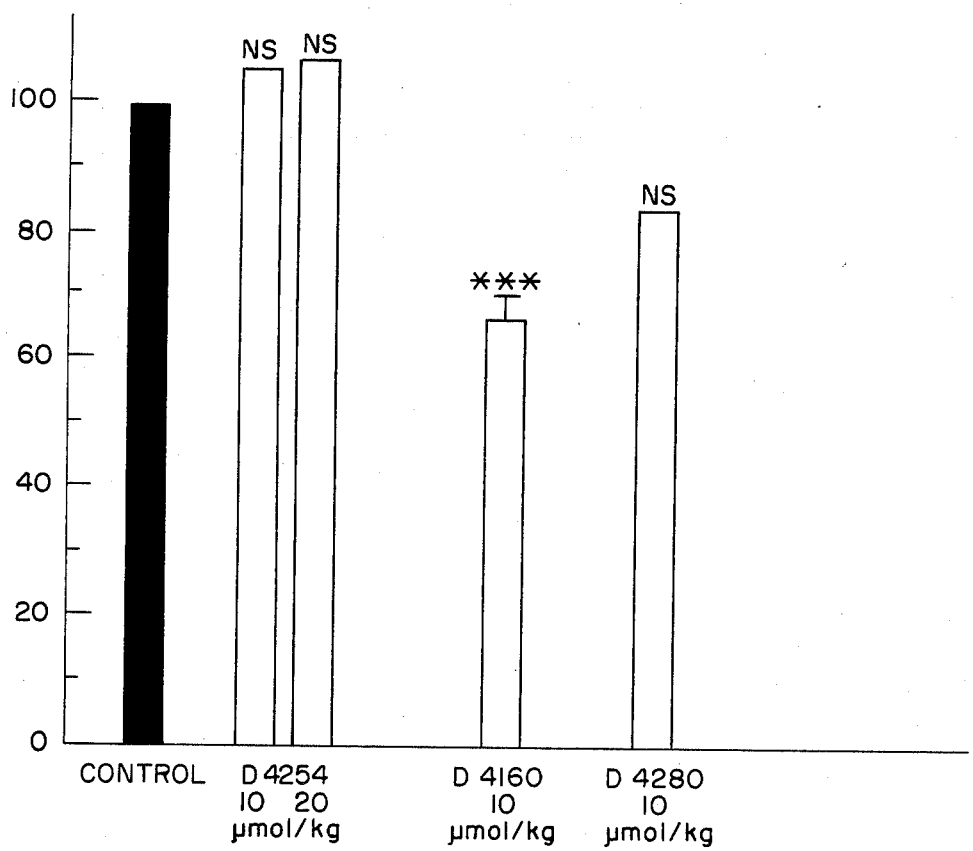

LOCOMOTOR ACTIVITY, MICE
(SUBCUTAN. ADMINISTRATION)

LEGEND TO FIGURE:

SPONTANEOUS MOTOR ACTIVITY HAS BEEN RECORDED DURING THE INITIAL ACTIVE PERIOD (5 MIN.) AFTER PLACING THE ANIMALS IN THE MOTRON ACTIVITY METER. AT EACH DOSE LEVEL, THREE GROUPS TOTALLING NINE MICE WERE USED. SEVEN GROUPS SERVED AS CONTROLS RECEIVING SALINE. BY GIVING THE DRUGS SUBCUTANEOUSLY (D 4160 WAS GIVEN INTRAPERITONEALLY) 30 MINUTES BEFORE RECORDING, A SUITABLE ABSORPTION TIME WAS ALLOWED FOR THE DRUGS TO PRODUCE OPTIMAL BEHAVIORAL EFFECTS. D 4280 PRODUCED MARKED IRRITATION WITH HAIR-LOSS AT THE INJECTION SITE. THIS IRRITATING ACTION INVALIDATED THE EVALUATION OF THIS COMPOUND.

BARS REPRESENT MEAN ± SEM.

NS = NOT SIGNIFICANTLY DIFFERENT FROM CONTROL ($p < 0.05$)
** = SIGNIFICANTLY DIFFERENT FROM CONTROL ($p < 0.01$)
*** = SIGNIFICANTLY DIFFERENT FROM CONTROL ($p\ 0.001$)

FIG. B

3,8-DIALKYLXANTHINES

This application is a continuation-in-part of application Ser. No. 248,995 filed Nov. 30, 1981, now abandoned.

BACKGROUND OF THE INVENTION

The present invention relates to novel, pharmacologically active compounds, methods for their preparation and their therapeutic use. The invention also relates to pharmaceutical compositions containing the compounds. More particularly, the novel compounds of the invention are intended for the treatment of chronic obstructive airway disease (COAD) and cardiovascular diseases.

Theophylline and various salts thereof are used in the treatment of chronic obstructive airway disease (COAD) and cardiac disease. Major therapeutic effects of theophylline are to relax bronchial smooth muscle and stimulate heart muscle. The major drawback with theophylline therapy is that the drug frequently produces toxic side effects; most common are nausea and gastric distress, most serious are convulsions, which may lead to death.

The object of the present invention is to provide xanthine derivatives which are more potent than theophylline. Another object of the present invention is to provide xanthine derivatives which have a bronchodilatory and cardiovascular potency, but which do not produce drowsiness.

Certain xanthine derivatives, in particular the 1,3,8-trialkylxanthines having a 1-methyl group combined with a group having 4–7 carbon atoms in the 3-position, are used in the treatment of bronchial asthma and other bronchospastic and allergic diseases. The major drawback with 1,3,8-trialkylxanthine therapy is that such drugs frequently produce behavioral side effects, such as drowsiness. Thus, a patient so treated must cope with an impaired level of alertness. In these instances, operation of heavy machinery or driving a car would be contraindicated.

SUMMARY OF THE INVENTION

It has been found according to the present invention that compounds of the formula

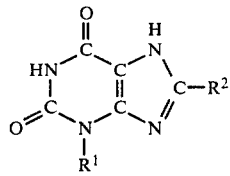

and the physiologically acceptable salts thereof, wherein $R^1$ is ethyl, n-propyl, n-butyl, isobutyl, n-pentyl, 2-methylbutyl, 3-methylbutyl, 2,2-dimethylpropyl, cyclopropyl, cyclobutyl, cyclopentyl or cyclohexylmethyl, and $R^2$ is methyl, ethyl, n-propyl, isopropyl, cyclopropyl, n-butyl, isobutyl, tert. butyl or cyclobutyl provided that $R^1$ is ethyl when $R^2$ is methyl, possess an increased bronchodilator and cardiovascular potency compared to theophylline, without causing drowsiness. These advantageous properties make the compounds of the invention valuable in the treatment of chronic obstructive airway disease (COAD) and of cardiovascular disease.

This invention also takes into consideration that compounds which structurally deviate from the formula (I) may be transformed after administration to a living organism to a compound of the formula (I) and in this structural form exert their effects. This consideration is a further aspect of this invention.

BRIEF DESCRIPTION OF THE DRAWING

FIG. A and B are graphs showing the effects of the claimed compounds and the prior art compounds on locomotor activity.

DISCLOSURE OF THE INVENTION

The present invention includes pharmaceutically acceptable salts of compounds of formula (I) with pharmaceutically acceptable bases. The term "pharmaceutically acceptable salts" means salts the cation of which are relatively innocuous to the animal organism when used in therapeutic doses so that the beneficial pharmacological properties of the parent compounds of general formula (I) are not vitiated by side effects ascribable to those cations. Suitable salts include alkali metals, e.g. sodium and potassium, and ammonium salts and salts of amines known in the art to be pharmaceutically acceptable, e.g. glycine, ethylene diamine, choline, diethanolamine, triethanolamine, octadecylamine, diethylamine, triethylamine, 1-amino-2-propanol-2-amino-2-(hydroxymethyl) propane-1,3-diol, and 1-(3,4-dihydroxyphenyl)-2-isopropylaminoethanol.

Pharmaceutically acceptable salts may be prepared by the reaction together of stoichiometric quantities of a compound of formula (I) and the appropriate base, that is to say, a base as described immediately hereinbefore, for example at an elevated temperature, with or without an appropriate solvent, preferably followed by recrystallization from an appropriate solvent, for example a hydroxylic solvent, e.g. water, of the salt so formed.

In clinical practice, the compounds of the present invention will normally be administered orally, rectally, nasally, sublingually, by injection or by inhalation in the form of a pharmaceutical preparation comprising the active ingredient in the form of the original compound or optionally in the form of a pharmaceutically acceptable carrier which may be a solid, semi-solid or liquid diluent or an ingestible capsule, and such preparations comprise a further aspect of the invention. Usually the active substance will comprise between 0.1 and 99% by weight of the preparation, for example between 0.5 and 20% for preparations intended for injection and between 0.1 and 50% for preparations intended for oral administration.

To produce pharmaceutical preparations in the form of dosage units for oral application containing a compound of the invention, the active ingredient may be mixed with a solid, pulverulent carrier, for example lactose, saccharose, sorbitol, mannitol, a starch such as potato starch, corn starch, amylopecin, laminaria powder or citrus pulp powder, a cellulose derivative, polyvinylpyrrolidone or gelatine and also may include lubricants such as magnesium or calcium stearate or a Carbowax ® or other polyethylene glycol waxes and compressed to form tablets or cores for dragées. If drag/ées are required, the cores may be coated, for example with concentrated sugar solutions which may contain gum arabic, talc and/or titanium dioxide, or alternatively with a film forming agent dissolved in easily volatile organic solvent or other suitable solvent or mixtures of organic solvents. Dyestuffs can be added to these coatings for example, to distinguish between different contents of active substance.

For the preparation of soft gelatine capsules (pearl-shaped closed capsules) consisting of gelatine and, for example, glycerol as a plasticizer, or similar closed capsules, the active substance may be admixed with a Carbowax ® or a suitable oil as e.g. sesame oil, olive oil, or arachis oil. Hard gelatine capsules may contain granulates of the active substance with solid, pulverulent carriers such as lactose, saccarose, sorbitol, mannitol, starches (for example potato starch, corn starch or amylopectin), cellulose derivatives, polyvinylpyrrolidine or gelatine and may also include magnesium stearate or stearic acid as lubricants.

A compound of the invention may also be formulated as a sustained action dosage form using suitable excipients. Different methods may be used for the availability control e.g. diffusion process and ion exchange. Methods using the diffusion process may be exemplified by products involving coated granules or particles, matrix imbedded drug and slightly soluble forms.

Effervescent powders are prepared by mixing the active ingredient with non-toxic carbonates or hydrogen carbonates of e.g. sodium, potassium or calcium, such as calcium carbonate, potassium carbonate and potassium hydrogen carbonate, solid, non-toxic acids such as tartaric acid, ascorbic acid, and citric acid, and for example aroma.

Liquid preparations for oral application may be in the form of elixirs, syrups or suspensions, for example, solutions containing from about 0.1% to 20% by weight of active substance, sugar and a mixture of ethanol, water, glycerol, propylene glycol and optionally aroma, saccharine and/or carboxymethylcellulose as a dispersing agent.

For parenteral application by injection preparations may comprise an aqueous solution or suspension of the active substances according to the invention, desirably in a concentration of 0.5–10%, and optionally also a stabilizing agent and/or buffer substances in aqueous solution. Dosage units of the solution may advantageously be enclosed in ampoules.

The dosage at which the active ingredients are administered may vary within a wide range and will depend on various factors such as, for example, the individual requirements of each patient. A suitable oral dosage range is from 50 to 1000 mg given 1 to 4 times a day. A suitable dosage range at parenteral administration is from 20 to 500 mg.

The pharmaceutical compositions containing the active ingredients may suitably be formulated so that they provide doses within these ranges either as single dosage units or as multiple dosage units.

The compounds of the invention can be prepared by any of the following methods:

A. Reacting a compound of the formula

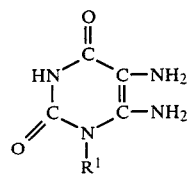

with a compound of the formula $$R^2-X$$

wherein $R^1$ is ethyl, n-propyl, n-butyl, isobutyl, n-pentyl, 2-methylbutyl, 3-methylbutyl, 2,2-dimethylpropyl, cyclopropyl, cyclobutyl, cyclopentyl, or cyclohexylmethyl, $R^2$ is methyl, ethyl, n-propyl, isopropyl, cyclopropyl, n-butyl, isobutyl, tert. butyl or cyclobutyl, X is —COOH, —CONH$_2$ or —OC—O—CO—R$^2$, provided that $R^1$ is ethyl when $R^2$ is methyl and, if necessary, submitting the obtained product to dehydration.

The dehydration may be carried out for instance by heating the reaction mixture in the absence of solvent or by heating the mixture with alkali or by boiling the mixture in a high-boiling solvent.

The starting material of the compounds prepared according to this route can be obtained for instance as illustrated in the reaction scheme below, wherein the radical $R^1$ has the meaning given in this specification.

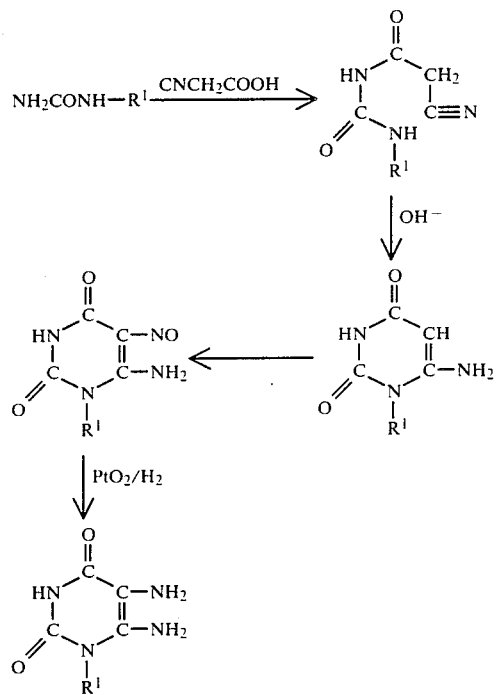

B. Reacting a compound of the formula

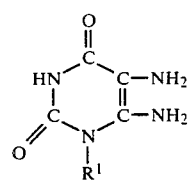

with a compound of the formula

wherein R is ethyl, n-propyl, n-butyl, isobutyl, n-pentyl, 2-methylbutyl, 3-methylbutyl, 2,2-dimethylpropyl, cyclopropyl, cyclobutyl, cyclopentyl, or cyclohexylmethyl, $R^2$ is methyl, ethyl, n-propyl, isopropyl, cyclopropyl, n-butyl, isobutyl, tert. butyl or cyclobutyl, $X^1$ is

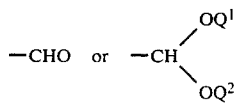

provided that $R^1$ is ethyl when $R^2$ is methyl, and submitting the obtained product to oxidative cyclization.

$Q^1$ is hydrogen or an alkyl group with 1-3 carbon atoms and $Q^2$ is an alkyl group with 1-3 carbon atoms. Preferably $Q^1$ and $Q^2$ are methyl or ethyl.

For the oxidative cyclization, a variety of agents can be used, e.g. thionyl chloride, $SOCl_2$. C. Reacting a compound of the formula

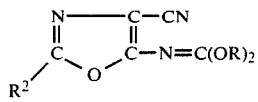

with a compound of the formula

wherein $R^1$ is ethyl, n-propyl, n-butyl, or n-pentyl, $R^2$ is methyl, ethyl, n-propyl, isopropyl, cyclopropyl, n-butyl, isobutyl, tert. butyl or cyclobutyl, R is a lower alkyl group (with 1-3 carbon atoms), provided that $R^1$ is ethyl when $R^2$ is methyl, and submitting the obtained product to a basic medium.

By this method, compounds of the formula (1) wherein $R^1$ is ethyl, n-propyl, n-butyl or n-pentyl, $R^2$ is methyl, ethyl, n-propyl, isopropyl, cyclopropyl, n-butyl, isobutyl, tert. butyl or cyclobutyl, provided that $R^1$ is ethyl when $R^2$ is methyl are obtained.

WORKING EXAMPLES

Example 1

Preparation of 3,7-dihydro-3-ethyl-8-methyl-1H-purine-2,6-dione VI D 4202

(a) Preparation of 6-amino-1-ethyl-2,4(1H,3H)-pyrimidinedione II.

120 g (1.36 mol) of ethylurea were added to a solution of 127.5 g (1.5 mol) cyanoacetic acid and 200 ml of acetic anhydride. The solution was stirred at 60°–70° C. for 2 hours. After cooling, white crystals were filtered off and washed with ethanol. Yield 153 g (74%) (I). This was stirred in 1 liter of hot water and 160 ml of 2N NaOH was added in portions so the solution was basic the whole time. The reaction mixture was refluxed for 20 minutes and then neutralized with 5N HCl. After cooling, white crystals were filtered off. Yield 100 g (65%) (II) NMR. (DMSOd6) 3H, 1.20 t; 2H, 3.97 m; 2H 7.03 s; 1H, 4.77 s; 1H, 10.50 s.

(b) Preparation of 6-amino-1-ethyl-5-nitroso-2,4-(1H,3H)-pyrimidinedione III.

145 ml of 5N HCl and 50 g of $NaNO_2$ (0.72 mol) which were dissolved in water were added to 100 g (0.65 mol) of 6-amino-1-ethyl-2,4-(1H,3H)-pyrimidinedione (II), dissolved in 1 liter hot water. After cooling the red crystals were filtered off and washed with water. Yield 97.7 g (83%) (III). NMR (DMSOd6) 3H, 1.27 t; 2H, 4.03 q; 1H, 9.30 b; 1H 11.63 b; 1H 13.50 s.

(c) Preparation of 5,6-diamino-1-ethyl-2,4(1H, 3H)-pyrimidinedione IV.

240 g of sodium dithionite in portions were added to a suspension of 97 g of 6-amino-1-ethyl-5-nitroso-2,4-(1H,3H)-pyrimidinedione (III). The pale red crystals were filtered off and washed with water. Yield 89 g (99%) IV. (DMSOd6) 3H, 1.23 t; 2H, 4.00 q; 2H, 2.50–3.70; 2H, 6.30 s.

(d) Preparation of 3,7-dihydro-3-ethyl-8-methyl-1H-purine-2,6-dione VI.

A solution of 82 g of 5,6-diamino-1-ethyl-2,4-(1H,3H)-pyrimidinedione (IV) in 200 ml of acetic acid was refluxed for 2 hours. The hot solution was added to 1 liter of acetone. The received crystals were filtered off. Yield 97.4 g V.

The amide (V) was refluxed in 300 ml of 2N NaOH for 1 hour and then neutralized with 5N HCl. The crystals were filtered off and washed with water and ethanol. Yield 57.8 g (62%). NMR (DMSOd6) 3H, 1.30 t; 2H, 410 q; 3H, 2.50 s; 1H, 10.97 s; 1H, 13.17 b.

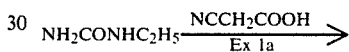

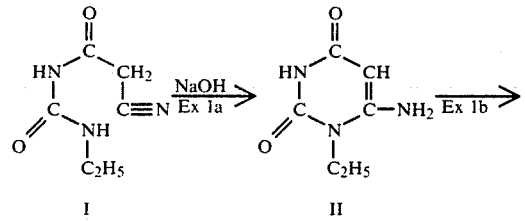

-continued

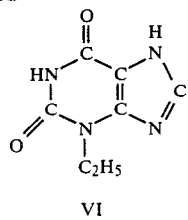
VI

Example 2

Preparation of 3,8-diethyl-3,7-dihydro-1H-purine-2,6-dione VII D 4236

A solution of 5 g of 5,6-diamino-1-ethyl-2,4-(1H,3H)-pyrimidinedione (IV) in 25 ml of propionic acid was refluxed for 2 hours. The hot solution was added to 50 ml of acetone. The received crystals were filtered off. Yield 5.4 g.

The amide was refluxed in 25 ml of 2N NaOH for 1 hour and then neutralized with 5N HCl. The crystals were filtered off and recrystallized from 40 ml of acetic acid. Yield 2.7 g (44%). NMR (DMSOd$_6$) 6H, 1.26 m; 2H, 2.77 q; 2H, 4.03 q; 1H, 10.93 s; 1H, 13.13 s.

Example 3

Preparation of 3,7-dihydro-8-ethyl-3-propyl-1H-purine-2,6-dione XIII D 4235

(a) Preparation of 6-amino-1-propyl-2,4-(1H,3H)-pyrimidinedione IX.

50 g (0.49 mol) of n-propylurea were added to a solution of 47 g (0.55 mol) cyanoacetic acid and 100 ml of acetic anhydride. The solution was stirred at 60°-70° C. for 1 hour. After cooling, white crystals were filtered off and washed with ethanol. Yield 56.2 g (68%) (VIII). This was stirred in 100 ml of hot water and 60 ml of 2N NaOH was added in portions so the solution was basic the whole time. The reaction mixture was refluxed for 20 minutes and then neutralized with 5N HCl. After cooling, white crystals were filtered off. Yield 34.3 g (61%) (IX) NMR.

(b) Preparation of 6-amino-5-nitroso-1-propyl-2,4-(1H,3H)-pyrimidinedione X.

45 ml of 5N HCl and 15 g of NaNO$_2$ (0.22 mol) which were dissolved in water were added to 34.3 g (0.20 mol) of 6-amino-1-propyl-2,4-(1H,3H)-pyrimidinedione (IX), dissolved in 900 ml hot water. After cooling, the red crystals were filtered off and washed with water. Yield 33.3 g (83%) (X) NMR.

(c) Preparation of 5,6-diamino-1-propyl-2,4-(1H,3H)-pyrimidinedione XI.

33.3 g of 6-amino-5-nitroso-1-propyl-2,4-(1H,3H)-pyrimidinedione (X) were catalytically hydrogenated in 800 ml of DMF and in the presence of 0.1 g PtO$_2$ for 3 hours and at room temperature and at a pressure of 200 kPa. The catalyst and the crystals were filtered off and washed with ethanol. Yield 29 g (93%) (XI).

(d) Preparation of 3,7-dihydro-8-ethyl-3-propyl-1H-purine-2,6-dione XIII.

A solution of 2.5 g of 5,6-diamino-1-propyl-2,4-(1H,3H)-pyrimidinedione (XI) in 20 ml of propionic acid was refluxed for 2 hours. The hot solution was filtered and 50 ml of acetone were added. The crystals which formed were then filtered off. Yield 2.0 g (XII).

The amide (XII) was refluxed in 25 ml of 2N NaOH for 2 hours and then neutralized with 5N HCl. The crystals were filtered off and recrystallized from 120 ml ethanol.

Yield 0.9 g (68%) (XIII). NMR (DMSOd$_6$) 3H, 0.97 q; 3H, 1.30 t; 2H, 1.73 m; 2H, 2.77 t; 2H, 3.93 t; 1H, 10.90 s; 1H, 13.23 b.

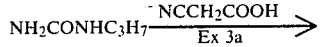

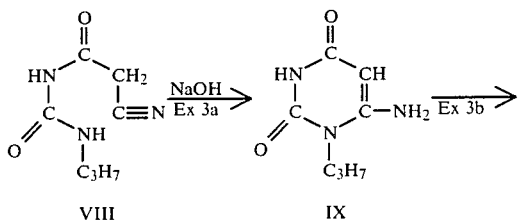
VIII    IX

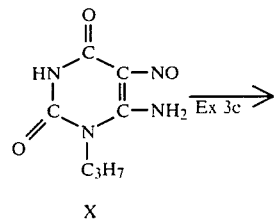
X

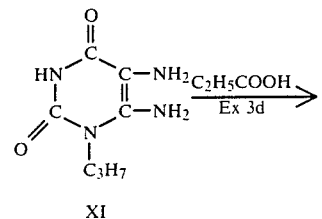
XI

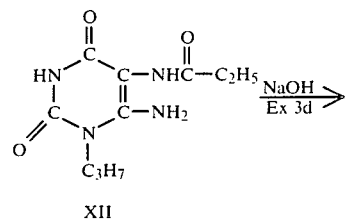
XII

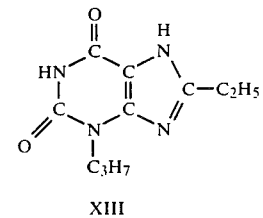
XIII

Example 4

In the same way as in Example 1 the compounds listed in Table 1 were prepared. The names of the starting urea and the names of the carboxylic acid used in the last step are listed in the fourth and fifth columns. In Table 2 the chemical names and in Table 3 NMR-data of the prepared compounds are given.

TABLE 1

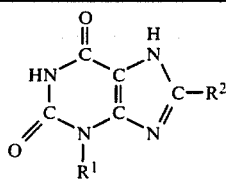

| Compound | R₁ | R₂ | urea | carboxylic acid | Yield % |
|---|---|---|---|---|---|
| D 4241 | ethyl | n-propyl | ethylurea | n-butyric acid | 42 |
| D 4246 | ethyl | isopropyl | ethylurea | isobutyric acid | 39 |
| D 4252 | ethyl | n-butyl | ethylurea | valerianic acid | 25 |
| D 4253 | ethyl | isobutyl | ethylurea | isovalerianic acid | 31 |
| D 4240 | n-propyl | n-propyl | propylurea | n-butyric acid | 34 |
| D 4245 | n-propyl | isopropyl | propylurea | isobutyric acid | 44 |
| D 4250 | n-propyl | cyclopropyl | propylurea | cyclopropylic acid | 17 |
| D 4248 | n-propyl | n-butyl | propylurea | valerianic acid | 21 |
| D 4249 | n-propyl | isobutyl | propylurea | isovalerianic acid | 33 |
| D 4266 | n-propyl | tert.-butyl | propylurea | pivalic acid | 29 |
| D 4251 | n-popyl | cyclobutyl | propylurea | cyclobutanic acid | 21 |
| D 4261 | n-butyl | ethyl | n-butylurea | propanoic acid | 35 |
| D 4257 | isobutyl | ethyl | isobutylurea | propanoic acid | 30 |
| D 4271 | n-pentyl | ethyl | n-pentylurea | propanoic acid | 15 |
| D 4254 | 3-methylbutyl | ethyl | 3-methylbutylurea | propanoic acid | 35 |
| D 4269 | cyclohexylmethyl | ethyl | cyclohexylurea | propanoic acid | 48 |
| D 4270 | 2,2-dimethylpropyl | ethyl | 2,2-dimethylpropylurea | propanoic acid | 36 |
| D 4267 | cyclopropyl | ethyl | cyclopropylurea | propanoic acid | 20 |
| D 4268 | cyclopropyl | propyl | cyclopropylurea | n-butyric acid | 10 |
| D 4277 | cyclopentyl | ethyl | cyclopentylurea | propanoic acid | 47 |

TABLE 2

Chemical names of compounds

| | |
|---|---|
| D 4241 | 3,7-Dihydro-3-ethyl-8-propyl-1H—purine-2,6-dione |
| D 4246 | 3,7-Dihydro-3-ethyl-8-isopropyl-1H—purine-2,6-dione |
| D 4252 | 8-Butyl-3,7-dihydro-3-ethyl-1H—purine-2,6-dione |
| D 4253 | 3,7-Dihydro-3-ethyl-8-isobutyl-1H—purine-2,6-dione |
| D 4240 | 3,7-Dihydro-3,8-dipropyl-1H—purine-2,6-dione |
| D 4245 | 3,7-Dihydro-8-isopropyl-3-propyl-1H—purine-2,6-dione |
| D 4250 | 8-Cyclopropyl-3,7-dihydro-3-propyl-1H—purine-2,6-dione |
| D 4248 | 8-Butyl-3,7-dihydro-3-propyl-1H—purine-2,6-dione |
| D 4249 | 3,7-Dihydro-8-isobutyl-3-propyl-1H—purine-2,6-dione |
| D 4266 | 3,7-Dihydro-8-(1,1-dimethylethyl)-3-propyl-1H—purine-2,6-dione |
| D 4251 | 8-Cyclobutyl-3,7-dihydro-3-propyl-1H—purine-2,6-dione |
| D 4261 | 3-Butyl-3,7-dihydro-8-ethyl-1H—purine-2,6-dione |
| D 4257 | 3,7-Dihydro-8-ethyl-3-isobutyl-1H—purine-2,6-dione |
| D 4271 | 3,7-Dihydro-8-ethyl-3-pentyl-1H—purine-2,6-dione |
| D 4254 | 3,7-Dihydro-8-ethyl-3-(3-methylbutyl)-1H—purine-2,6-dione |
| D 4269 | 3-Cyclohexylmethyl-3,7-dihydro-8-ethyl-1H—purine-2,6-dione |
| D 4270 | 3,7-Dihydro-3-(2,2-dimethylpropyl)-8-ethyl-1H—purine-2,6-dione |
| D 4267 | 3-Cyclopropyl-3,7-dihydro-8-ethyl-1H—purine-2,6-dione |
| D 4268 | 3-Cyclopropyl-3,7-dihydro-8-propyl-1H—purine-2,6-dione |
| D 4277 | 3-Cylcopentyl-3,7-dihydro-8-ethyl-1H—purine-2,6-dione |
| a/ | 3,7-Dihydro-8-ethyl-3-(2-methylbutyl)-1H—purine-2,6-dione |
| b/ | 3-Cyclobutyl-3,7-dihydro-8-ethyl-1H—purine-2,6-dione |

TABLE 3

NMR-shift data
Solvent DMSO $d_6$ ($\delta$ = 2.60)

| | |
|---|---|
| D 4241 | 3H 0.93 t, 3H 1.23 t, 2H 1.77 m, 2H 2.73 t, 2H 4.03 q, 1H 11.0 s, 1H 13.20 s |
| D 4246 | 3H 1.30 t, 6H 1.36 d, 1H 3.18 m, 2H 4.06 q. 1H 11.06 s, 1H 13.00 s |
| D 4252 | 3H 1.23 t, 7H 1.33 m, 2H 2.73 t, 2H 4.00 q, 1H 11.00 s, 1H 13.20 s |
| D 4253 | 6H 1.00 d, 3H 1.30 t, 1H 2.17 m, 2H 2.67 d, 2H 4.06 q, 1H 11.03 s, 1H 13.20 s |
| D 4240 | 6H 0.97 t, 4H 1.73 m, 2H 2.73 t, 2H 3.93 t, 1H 11.10 s, 1H 13.26 s |
| D 4245 | 3H 0.90 t, 6H 1.30 d, 2H 1.73 m, 1H 3.10 m, 2H 3.96 t, 1H 10.96 s, 1H 13.10 s |
| D 4250 | 3H 0.86 t, 4H 1.00 m, 2H 1.70 m, 1H 2.03 m, 2H 4.03 t, 1H 10.83 s, 1H 13.07 s |
| D 4248 | 3H 0.86 t, 4H 1.47 m, 2H 1.63 m, 2H 2.70 t, 2H 3.93 t, 1H 10.96 s, 1H 13.13 s |
| D 4249 | 3H 0.83 t, 6H 0.93 d, 2H 1.70 m, 1H 2.03 m, 2H 2.53 d, 2H 3.93 t, 1H 10.93 s, 1H 13.10 s |
| D 4266 | 3H 0.93 t, 9H 1.40 s, 2H 1.77 m, 2H 4.03 t, 1H 10.53 s |
| D 4251 | 3H 0.90 t, 2H 1.80 m, 4H 2.23 m, 2H 4.00 t, 1H 10.96 s, 1H 13.16 s |
| D 4261 | 3H 0.97 t, 3H 1.30 t, 4H 1.60 m, 2H 2.83 q 2H 3.70 t, 1H 11.03 s, 1H 13.23 s |
| D 4257 | 6H 0.90 d, 2H 1.26 t, 1H 2.30 m, 2H 2.80 q, 2H 3.87 d, 1H 11.00 s, 1H 13.10 s |
| D 4271 | 3H 0.87 t, 3H 1.30 t, 6H 1.53 m, 2H 2.80 q, 2H 4.00 t, 1H 11.07 s, 1H 13.20 br |
| D 4254 | 8H 0.93 m, 3H 1.30 t, 1H 2.07 m, 2H 2.80 q, 2H 3.90 d, 1H 11.00 s, 1H 13.17 br |
| D 4269 | 3H 1.33 t, 10H 1.43 b, 2H 2.83 q, 2H 3.87 d, 1H 11.07 s |
| D 4270 | 9H 1.00 s, 3H 1.27 t, 2H 2.77 q, 2H 3.90 s, 1H 11.07 s, 1H 13.20 br |
| D 4267 | 4H 1.07 m, 3H 1.33 t, 2H 2.80 q, 1H 2.97 m, 1H 11.10 s, 1H 13.27 br |
| D 4268 | 7H 1.00 m, 2H 1.80 m, 2H 2.73 m, 1H 2.97 m, 1H 10.93 s, 1H 13.20 br |
| D 4277 | 8H 1.97 m, 3H 1.33 t, 2H 2.80 q, 1H 5.27 m |

The following Examples illustrate how the compounds of the invention can be incorporated in pharmaceutical compositions.

Example 5

Aerosol for inhalation

| | |
|---|---|
| Active substance | 1.50 g |
| "Miglyol" (Registered Trade Mark) | 0.20 g |
| "Frigen" (Registered Trade Mark) 11/12/113/114 ad | 100.0 g |

"Frigen" is used to denote the halogenated hydrocarbons. "Frigen" 114 is 1,2-dichloro-1,1,2,2-tetrafluroethane. "Frigen" 113 is 1,1-difluoro-2,2-dichlorotrifluorotrichloroethane. "Frigen" 11 is trichloromonofluoromethane and "Frigen" 12 is dichlorodifluoromethane. "Miglyol" denotes a triglyceride of saturated vegetable oils, or a pulver aerosol where the active substance is mixed with lactose.

Example 6

Tablets

| Each tablet contains: | |
|---|---|
| Active substance | 20.0 mg |
| Maize starch | 25.0 mg |
| Lactose | 190.0 mg |
| Gelatin | 1.5 mg |
| Talc | 12.0 mg |
| Magnesium stearate | 1.5 mg |
| | 250.0 mg |

Example 7

Suppositories

Each suppository contains

| | |
|---|---|
| Active substance | 50.0 mg |
| Ascorbyl palmitate | 1.0 mg |
| Suppository base (Imhausen H) ad | 2,000.0 mg |

Example 8

Injection solution

| | |
|---|---|
| Active substance | 2.000 mg |
| Sodium hydroxide | 0.310 mg |
| Sodium purosulphite | 0.500 mg |
| Disodium edetate | 0.100 mg |
| Sodium chloride | 8.500 mg |
| Sterile water for injection ad | 1.00 g |

Example 9

Sublingual tablets

| Each tablet contains: | |
|---|---|
| Active substance | 20.0 mg |
| Lactose | 85.0 mg |
| Agar | 5.0 mg |
| Talc | 5.0 mg |

PHARMACOLOGICAL TESTS

Isolated Guinea-pig Trachea

Guinea-pigs of both sexes, weighing between 150 and 250 g, were killed by a blow on the head and bled. The trachea was removed and cut spirally yielding one or two preparations. The tracheal preparations were mounted in organ baths containing Krebs solution maintained at 37° C. and bubbled with carbogen (95% $O_2$ + %5 $CO_2$).

Isometric tension reflecting mainly the activity in circular tracheal muscle was recorded by means of a force displacement transducer. Initial tension was set at 0.5 g which was the approximate basal tension kept during the experiment. Evaluation of relaxant effects was made when the preparation had contracted to a stable tension by the addition of carbacholine 0.1 ug/ml to the bath. $EC_{50}$ values, i.e. molar concentrations of xanthines required to produce 50% maximum response, were obtained from log concentration response lines and used to calculate the potency of theophylline relative to that of the test drug.

After washing out the drugs the trachea resumed its basal tone and was left to stabilize for at least 15 minutes before the next drug evaluation was performed. Between two evaluations of theophylline the effect of the test drugs was examined and its $EC_{50}$ value was compared with the mean of the previous and following $EC_{50}$ values of theophylline. The potency ratios are illustrated in Table 4. Theophylline is one by definition and a value larger than one indicates that the drug is more potent than theophylline.

TABLE 4

| Compound | Guinea-pig trachea Potency ratio of theophylline |
|---|---|
| D 4202 | 1.7 |
| D 4236 | 4.5 |
| D 4241 | 5.8 |
| D 4246 | 4.5 |
| D 4252 | 8.2 |
| D 4253 | 5.4 |
| D 4235 | 3.9 |
| D 4240 | 7.5 |
| D 4245 | 4.9 |
| D 4250 | 7.1 |
| D 4248 | 8.5 |
| D 4249 | 3.5 |
| D 4251 | 8.9 |
| D 4261 | 2.7 |
| D 4257 | 3.1 |
| D 4271 | 6.7 |
| D 4254 | 4.4 |
| D 4270 | 2.6 |
| D 4267 | 1.4 |
| D 4268 | 2.2 |

Legend to Table

The column lists molar potency ratios for bronchodilatation between thophylline and selected xanthine compounds.

LOCOMOTOR ACTIVITY STUDIES IN MICE

Tests were carried out with respect to important side effects of the compounds of this invention. Specifically, it is known that some xanthines produce a sedative effect which can influence general alertness levels. Compounds having such sedative effects are undesirable because they impair the ability to perform tasks which require alertness, for example, car-driving.

The sedative effects of the compounds of this invention were compared with those of the xanthines disclosed by U.S. Pat. Nos. 4,089,959 and 4,233,303. Mice were injected both with saline (as a control) and with test compounds and the effects on spontaneous motor activity were observed. The drugs were administered subcutaneously 30 minutes before the commencement of measurement to provide a suitable absorption period to produce optimal behavioral effects. After 30 minutes, the mice were placed in a Motron Activity Meter.

The test results are shown in FIGS. A and B. In FIGS. A and B the black bar at the extreme left-hand side shows the response of the test mice which received only saline as a control. These control groups provide a bench mark for determining the normal level of spontaneous motor activity. The bars for the claimed compounds D 4277, D 4236 and D 4254 represent the results of dosing mice at the studied dose levels of 10 or 20 micromoles/kg. As can be seen, none of the compounds elicited a large reduction in spontaneous motor activity.

The bars for the compounds D 4136 [3-cyclopentyl-3,7-dihydro-1,8-dimethyl-1H-purine-2,6-dione], D 4026 [3,7-dihydro-1,6-dimethyl-3-phenyl-1H-purine-2,6-dione], D 4160 [3,7-dihydro-1,8-dimethyl-3-(2-methylbutyl)-1H-purine-2,6-dione] and D 4280 [3,7-dihydro-8-ethyl-1-methyl-3-(2-methylbutyl)-1H-purine-2,6-dione] represent the results from mice dosed with the compounds of the prior art, also at levels of 10 or 20 micromoles/kg. The prior art compounds, with the exception of D 4280 (see Legend to FIG. B), elicited a noticeable reduction in spontaneous locomotor activity, which indicates that they have a sedative effect.

BEST MODE OF CARRYING OUT THE INVENTION

Among the compounds of the present invention according to formula (I), the compounds 3,7-dihydro-3-ethyl-8-methyl-1H-purine-2,6-dione; 3,8-diethyl-3,7-dihydro-1H-purine-2,6-dione and 3,7-dihydro-8-ethyl-3-propyl-1H-purine-2,6-dione represent the best mode known at present.

We claim:
1. A compound of the formula

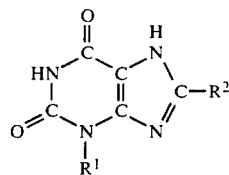

or a physiologically acceptable salt thereof, in which formula $R^1$ is ethyl, n-propyl, n-butyl, isobutyl, n-pentyl, 2-methylbutyl, 3-methylbutyl, 2,2-dimethylpropyl, cyclopropyl, cyclobutyl, or cyclopentyl and $R^2$ is methyl, ethyl, n-propyl, isopropyl, cyclopropyl, n-butyl, isobutyl, tert. butyl or cyclobutyl provided that $R^1$ is ethyl when $R^2$ is methyl;
when $R^2$ is ethyl, $R^1$ is ethyl, n-propyl, n-butyl, isobutyl, n-pentyl, 2-methylbutyl, 3-methylbutyl, 2,2-dimethylpropyl, cyclopropyl, cyclobutyl, or cyclopentyl;
when $R^2$ is n-propyl, $R^1$ is ethyl, n-propyl, or cyclopropyl;
when $R^2$ is isopropyl, $R^1$ is ethyl or n-propyl;
when $R^2$ is cyclopropyl, $R^1$ is n-propyl;
when $R^2$ is n-butyl, $R^1$ is ethyl or n-propyl;
when $R^2$ is isobutyl, $R^1$ is ethyl or n-propyl;
when $R^2$ is tert. butyl, $R^1$ is n-propyl; and
when $R^2$ is cyclobutyl, $R^1$ is n-propyl.

2. A compound according to claim 1 with the formula

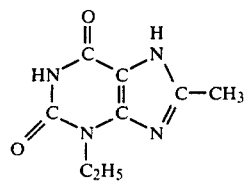

or a physiologically acceptable salt thereof.

3. A compound according to claim 1 with the formula

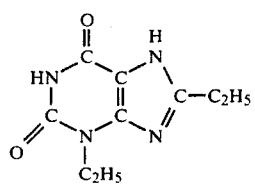

or a physiologically acceptable salt thereof.

4. A compound according to claim 1 with the formula

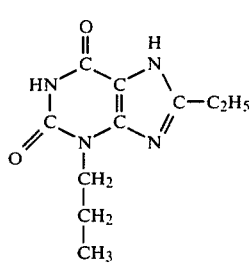

or a physiologically acceptable salt thereof.

* * * * *

UNITED STATES PATENT AND TRADEMARK OFFICE
CERTIFICATE OF CORRECTION

PATENT NO. : 4,546,182
DATED : 10-8-85
INVENTOR(S) : Kjellin et al.

It is certified that error appears in the above-identified patent and that said Letters Patent is hereby corrected as shown below:

Col. 1, line 5, "Nov. 30" should read --Mar. 30--;

Col 2, line 65, "drag/ées" should read --dragées--;

Col. 5, line 23, "C. Reacting a" should start a new paragraph at the lefthand margin;

Col. 9, TABLE I, 11th item under col. headed "$R_1$", "n-popyl" should read --n-propyl--;

Col. 11, lines 8 & 9, "'Frigen' (Registered Trade Mark 100.g 11/12/113/114 ad" should read --"Frigen" (Registered Trade Mark) 11/12/113/114   ad 100.g--; and Col. 11, line 50, "Sterile water for injection ad       1.00 g" should read --Sterile water for injection       ad 1.00 g--.

Signed and Sealed this

Twenty-fifth Day of February 1986

[SEAL]

Attest:

DONALD J. QUIGG

Attesting Officer

Commissioner of Patents and Trademarks